(12) United States Patent
Yang et al.

(10) Patent No.: US 10,172,842 B2
(45) Date of Patent: Jan. 8, 2019

(54) SUSTAINED RELEASE ORAL DOSAGE FORM CONTAINING DALFAMPRIDINE

(71) Applicant: PharmaDax Inc., New Taipei (TW)

(72) Inventors: Chih-Yao Yang, New Taipei (TW); Jen-Sen Wu, Taipei (TW); Shih-Wei Huang, New Taipei (TW); Yi-Chen Tsai, Taipei (TW); Chieh-Wen Chang, Taipei (TW); Cheng-Wei Chang, Tainan (TW)

(73) Assignee: PharmaDax Inc., New Taipei (TW)

( * ) Notice: Subject to any disclaimer, the term of this patent is extended or adjusted under 35 U.S.C. 154(b) by 0 days.

(21) Appl. No.: 15/256,636

(22) Filed: Sep. 5, 2016

(65) Prior Publication Data

US 2017/0071923 A1 Mar. 16, 2017

Related U.S. Application Data

(60) Provisional application No. 62/217,049, filed on Sep. 11, 2015.

(51) Int. Cl.
*A61K 31/4409* (2006.01)
*A61K 9/00* (2006.01)
*A61K 9/20* (2006.01)
*A61K 9/28* (2006.01)

(52) U.S. Cl.
CPC ........ *A61K 31/4409* (2013.01); *A61K 9/0004* (2013.01); *A61K 9/2009* (2013.01); *A61K 9/2027* (2013.01); *A61K 9/2031* (2013.01); *A61K 9/2072* (2013.01); *A61K 9/2866* (2013.01); *A61K 9/2853* (2013.01)

(58) Field of Classification Search
CPC .............. A61K 31/4409; A61K 9/0004; A61K 9/0053; A61K 9/2009; A61K 9/2013; A61K 9/2027; A61K 9/2031; A61K 9/2072; A61K 9/28; A61K 9/2853; A61K 9/2866
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 5,540,938 A | 7/1996 | Masterson et al. | |
| 8,007,826 B2 | 8/2011 | Blight et al. | |
| 8,354,437 B2 | 1/2013 | Blight et al. | |
| 8,440,703 B2 | 5/2013 | Blight et al. | |
| 8,663,685 B2 | 3/2014 | Blight et al. | |
| 8,877,935 B2 | 11/2014 | Garavaglia et al. | |
| 2002/0132005 A1* | 9/2002 | Faour .................. | A61K 9/0004 424/473 |
| 2006/0165798 A1* | 7/2006 | Edgren ................ | A61K 9/0004 424/473 |
| 2010/0272796 A1 | 10/2010 | Cunningham et al. | |
| 2012/0171287 A1* | 7/2012 | Jiang ..................... | A61K 9/0004 424/468 |
| 2015/0064234 A1* | 3/2015 | McCabe ............. | A61K 31/4409 424/450 |
| 2016/0081992 A1 | 3/2016 | Cunningham et al. | |
| 2016/0175294 A1 | 6/2016 | Cunningham et al. | |

FOREIGN PATENT DOCUMENTS

| | | | |
|---|---|---|---|
| CA | 2554697 A1 * | 4/2007 | ........... A61K 9/0004 |
| CN | 101896182 A | 11/2010 | |
| CN | 102018682 A | 4/2011 | |
| CN | 102442942 A | 5/2012 | |
| CN | 104220072 A | 12/2014 | |
| CN | 104334174 A | 2/2015 | |
| CN | 108451953 A | 8/2018 | |

OTHER PUBLICATIONS

Janssen. "OROS® Technology—INVEGA® (paliperidone)". Retrieved on Oct. 10, 2017. Retrieved from the internet <URL: http://www.janssencns.com/invega/schizoaffective-disorder/dosing-and-administration/oros-technology>; pp. 1-4.*
J. Evenhuis et al., "Pharmacokinetics of 4-aminopyridine in human volunteers: a preliminary study using a new GLC method for its estimation," Br J Anaesth, 53, pp. 567-570, 1981.
Donald R. A. Uges et al., "4-Aminopyridine kinetics," Clinical Pharmacology and Therapeutics, vol. 31, Issue 5, pp. 587-593, May 1982.
K. C. Hayes et al., "Pharmacokinetics of an Immediate-Release Oral Formulation of Fampridine (4-Aminopyridine) in Normal Subjects and Patients with Spinal Cord Injury," Journal of Clinical Pharmacology, vol. 43, pp. 379-385, 2003.
Andrew R. Blight et al., "Pharmacokinetics of 14C—radioactivity after oral intake of a single dose of 14C—labeled fampridine (4-aminopyridine) in healthy volunteers," Clinical Therapeutics, vol. 31, No. 2, pp. 328-335, 2009.
Oscar Fernandez et al., "Historical overview of the rationale for the pharmacological use of prolonged-release fampridine in multiple sclerosis," Expert Rev. Clin. Pharmacol., 5(6), pp. 649-665, 2012.
David R. Cornblath et al., "The Safety Profile of Dalfampridine Extended Release in Multiple Sclerosis Clinical Trials," Clinical Therapeutics, vol. 34, No. 5, pp. 1056-1069, 2012.

(Continued)

*Primary Examiner* — Doan T Phan

(74) *Attorney, Agent, or Firm* — CKC & Partners Co., Ltd.

(57) ABSTRACT

The present invention provides a sustained release oral dosage form containing dalfampridine that can be administered once daily. The dosage form includes dalfampridine as the active pharmaceutical ingredient and the excipients comprising osmotic agents in a tablet core. The sustained release oral dosage form of the present invention can be administrated once daily and can provide a proper fluctuation index to reduce undesired adverse effect, prevent alcohol-induced dose dumping and release drug at a rate sufficient to maintain certain drug plasma concentration.

14 Claims, No Drawings

(56) References Cited

OTHER PUBLICATIONS

Scott Weir et al., "Pharmacokinetic profile of dalfampridine extended release: clinical relevance in patients with multiple sclerosis," Current Medical Research and Opinion, vol. 29, No. 12, p. 1627-1636, 2013.
Scott Weir et al., "Population pharmacokinetics and pharmacodynamics of dalfampridine-ER in healthy volunteers and in patients with multiple sclerosis," Current Medical Research and Opinion, vol. 29, No. 12, pp. 1637-1645, 2013.
Ajaz S. Hussain, Ph.D., "Mitigating the Risk Posed by Alcohol-induced Dose Dumping," Presentations at the Pharmaceutical Sciences Advisory Committee Meeting Oct. 26, 2005.

* cited by examiner

SUSTAINED RELEASE ORAL DOSAGE FORM CONTAINING DALFAMPRIDINE

RELATED APPLICATIONS

This application claims priority to U.S. Provisional Application Ser. No. 62/217,049, filed Sep. 11, 2015, which is herein incorporated by reference.

BACKGROUND OF THE INVENTION

Field of Invention

The present invention relates to sustained release oral dosage form of a dalfampridine pharmaceutical tablet that can be administered once daily.

Description of Related Art

Dalfampridine, also named as 4-aminopyridine, 4-AP, or fampridine, is an organic compound with the chemical formula $C_5H_4N$—$NH_2$. It is used as a research tool, in characterizing subtypes of the potassium channel. It has also been used as a drug, to manage some of the symptoms of multiple sclerosis (MS), and is indicated for symptomatic improvement of walking in adults with several variations of the disease.

The safety and effectivity of dalfampridine are highly concerned. In clinical trials of dalfampridine extended release tablets in patients with MS, the incidence of seizures appeared to be dose related. Furthermore, dalfampridine plasma concentrations measured in patients who have experienced seizure have ranged from 104 to 475 ng/mL, which further suggesting that seizure incidence appears to be dose dependent. Although it is difficult to determine the temporal proximity of the dalfampridine plasma measurements to the initiation of seizure activity, it appears that a plasma dalfampridine concentration of approximately 100 ng/mL may be considered a likely threshold for increased risk of seizure in the absence of other risk factors (Clin Ther., 2012, 34(5), 1056-1069). In addition, it has been reported that if plasma concentrations were lower than 13 ng/mL, low percentage changes in walking speed in MS patients were observed; 13 ng/mL is equivalent to the average trough concentration achieved with 10 mg extended release tablets, twice daily (Current Medical Research & Opinion Vol. 29, No. 12, 2013, 1627-1636).

The approved drug product in the United States, AMPYRA®, is an extended release tablet designed for twice-daily oral administration. Each tablet contains 10 mg active pharmaceutical ingredient which is dalfampridine and comprises a rate-controlling polymeric matrix comprising of a hydrogel matrix, such as hydroxypropyl methylcellulose, which, when wet, will swell to form a hydrogel thus the rate of release of dalfampridine from this dosage formulation is sustained both by diffusion from the swollen tablet mass and by erosion of the tablet surface over time. The rate of release of dalfampridine may be controlled both by the amount of polymer per tablet and by the inherent viscosities of the polymers used.

However, the administration of the current marketed product, AMPYRA®, should be tightly managed with an approximately 12-hours interval between doses to avoid potential adverse effects, such as seizure. In addition, the drug release profile of a hydrogel matrix system is susceptible to food ingestion and usually results in burst plasma drug concentration, which may cause undesired adverse effects. Besides, the convenience of once daily administration will improve patient compliance and enhances therapeutic effect. Therefore, there is a need to have a dosage form that can provide a steady drug release profile with once daily oral administration of dalfampridine.

SUMMARY OF INVENTION

The present invention provides a sustained release oral dosage form containing dalfampridine that can be orally administered with once daily regimen in order to improve patient compliance and enhance therapeutic effect. The present invention also provides an oral dosage form is formulated as an osmotic tablet which provides a proper fluctuation index to avoid potential adverse effect.

In the present invention, the sustained release oral dosage form has a tablet core and a semipermeable membrane. The tablet core comprises dalfampridine, osmotic agents and expandable materials, and is formed as a multi-compartments system wherein at least one drug compartment comprises dalfampridine and at least one push compartment; or the tablet core is alternatively formed as a single compartment system wherein those materials are mixed within such compartment; or the tablet core is alternatively having a polymer compartment comprising at least one polymer located between drug compartment and push compartment, moreover, the polymer compartment optionally comprises dalfampridine. The polymer can be but not limited to hydroxypropyl methylcellulose, ethylcellulose, or co-polymers of acrylic and methacrylic acid esters. Furthermore, at least one passageway is located at the semipermeable membrane for releasing drug.

In the present invention, the sustained release oral dosage form comprises from 5 mg to 30 mg of dalfampridine and provides prolonged release of the drug for at least 18 hours, and optionally has an initial lag phase of drug release less than 2 hours after oral administration. Based on the results of pharmacokinetic (PK) simulation for certain examples, the oral dosage form of present invention provides a flattened drug plasma profile and maintains the drug plasma concentration at about 5 to 100 ng/mL for about 3 to 21 hours after oral administration. The drug release profile is not adversely influenced by factors such as pH of the medium, gastrointestinal peristalsis and food or alcohol intake. The oral dosage form provides a $C_{max}$ less than 100 ng/mL, a $T_{max}$ of about 8 hours or more than 8 hours, and moreover, an $AUC_{0-inf}$ in the range of 150 to 750 ng·h/mL. Furthermore, the oral dosage form provides a proper fluctuation index of about 1.5 or less.

In the present invention, the sustained release oral dosage form comprising dalfampridine to treat various neurological diseases, such as spinal cord injury, Alzheimer's disease, multiple sclerosis, amyotrophic lateral sclerosis or post-stroke deficiency.

It is to be understood that both the foregoing general description and the following detailed description are by examples, and are intended to provide further explanation of the invention as claimed.

DETAILED DESCRIPTION

The following terms shall be used to describe the present invention. In instances where a term is not specifically defined herein, the term shall be accorded its meaning, within the context of its use, as understood by person skilled in the art.

The term "about", "approximately" and the like, when used in connection with numerical variable, generally refers to the value of the variable and to all values of the variable that are within the experimental error.

The term "drug" refers to a pharmacologically active substance that, or so called active pharmaceutical ingredient, when delivered into a living organism, produces a desired, usually beneficial, effect. In the present invention the drug refers to dalfampridine or its derivatives that include but are not limited to pharmaceutically acceptable salt, ester, complex, chelate, clathrate, racemate, or enantiomer thereof. Although a limited number of drugs are represented in the exemplary embodiments herein, the invention is not to be limited by the exemplary embodiments but is fully applicable to other suitable drugs as would be understood by person skilled in the art.

The term "oral dosage form" refers to a dosage form that is delivered through mouth and can be but not limited to tablet, capsule, granule, powder, buccal film, sublingual film, oral paste, suspension, emulsion or syrup. In the present invention, the oral dosage form is preferably a tablet.

The term "excipient" refers to a pharmaceutically acceptable inactive substance for the purpose of bulking-up formulations that contain drug ingredients. It may be but not limited to binder, disintegrant, filler, film former, flavor, colorant, lubricant, glidant, sorbent, preservative, release rate controller or sweetener.

The term "release rate" refers to the quantity of drug released from a dosage form per unit time, e.g., milligrams of drug released per hour (mg/hr). Drug release rates are calculated under in vitro dosage form dissolution testing conditions known in the art. As used herein, a drug release rate obtained at a specified time refers to the in vitro drug release rate obtained at the specified time following implementation of an appropriate dissolution test. The dissolution test utilized in the Examples described herein were performed on dosage forms placed in a USP Type II dissolution machine and immersed in about 500 mL of purified water equilibrated in a constant temperature water bath at 37° C.±0.5° C. Aliquots of the release rate solutions were injected into a chromatographic system to quantify the amounts of drug released during the testing intervals.

An "immediate-release" dose of a drug refers to a dose that is substantially completely released within a time period of about 2 hours or 1 hour or less and, preferably, about 30 minutes or less. An immediate-release dose of drug applied as a coating on the surface of the oral dosage form, as used herein, refers to a dose of a drug prepared in a suitable pharmaceutically acceptable carrier to form a coating solution that will dissolve rapidly upon administration to thereby provide an immediate-release dose of drug. As is known in the art, such immediate-release drug overcoats may contain the same or a different drug or drugs as is contained within the underlying dosage form.

A "sustained-release" dose of a drug refers to a dose that is substantially completely released over an extended period of time, such as more than 18 hours, 20 hours or more than 24 hours.

The term "semipermeable membrane" refers to a membrane that permits the influx of a liquid from the exterior of the delivery device to the interior of the delivery device, and substantially impermeable to the passage of active agent from the tablet core.

The term "passageway" as used herein comprises means and methods suitable for releasing the agents from the oral dosage form. Other expression of such term includes aperture, orifice or bore through membrane formed by hand drilled, laser drilled, or mechanically drilled, or by eroding an erodible element, such as gelatin plug, in the environment of use. A detailed description of passageways and the maximum and minimum dimensions for a passageway are disclosed in U.S. Pat. Nos. 3,845,770 and 3,916,899. Generally, the diameter of passageway is preferred in the range of 0.02 to 2.0 mm.

The term "osmotic agent" refers to a material which creates an osmotic pressure within the oral dosage form which adopted the osmotic system. Upon penetration of fluid into the oral dosage form through semipermeable membrane, osmotic agents are dissolved in the fluid, which creates an osmotic gradient and generates a driving force for the uptake of fluid. Osmotic agents usually are ionic compounds which include but not limited to water-soluble salts, hydrophilic polymers, carbohydrates and water-soluble amino acids.

As noted above, the sustained release oral dosage form comprises a tablet core and a semipermeable membrane, wherein the tablet core comprises an active pharmaceutical ingredient or pharmaceutically acceptable salt thereof and the excipients, and is formed as a multi-compartments system or a single compartment system. Regarding to the multi-compartments system, it has at least one drug compartment and at least one push compartment. The active pharmaceutical ingredient is dalfampridine or its derivatives that include but are not limited to pharmaceutically acceptable salt, ester, complex, chelate, clathrate, racemate, or enantiomer thereof. In the present invention, the dosage form contains 5 mg to 30 mg, preferably 10 mg to 30 mg, more preferably 15 mg to 30 mg of dalfampridine. Dalfampridine is a known compound and could be prepared using known methods. In a method proposed by Fabio Garavaglia et al., the process for the preparation of dalfampridine was converting 4-pyridinecarbonitrile to dalfampridine by reacting 4-pyridinecarbonitrile with an oxidizing agent in the presence of a base without isolating any intermediate. See U.S. Pat. No. 8,877,935.

The excipients in the sustained release oral dosage form comprise osmotic agents and expandable materials. As noted above, the osmotic agent usually is ionic compounds which include but are not limited to water-soluble salts, hydrophilic polymers, carbohydrates and water-soluble amino acids. The osmotic agent may be selected from the group consisting of magnesium chloride, magnesium sulfate, lithium chloride, sodium chloride, sodium sulfate, sodium phosphate, potassium chloride, potassium sulfate, potassium phosphate, sodium acetate, potassium acetate, magnesium succinate, sodium benzoate, sodium citrate, sodium ascorbate, sodium carboxymethyl cellulose, hydroxypropyl methylcellulose, hydroxyethyl methylcellulose, methylcellulose, polyethylene oxide, polyvinylpyrrollidone, sucrose, sorbitol, mannitol, glucose, lactose, fructose, dextrose, glycine, leucine, alanine, methionine, urea or a combination thereof. The expandable materials for expanding, occupying an increasing area of the compartment. The expandable materials may be but not limited to the osmopolymer which is a polymer that can interact with water and aqueous fluids and swell or expand to an equilibrium state. The expandable materials may be selected from the group consisting of poly(methyl methacrylate), microcrystalline cellulose, methylcellulose, hydroxypropyl cellulose, hydroxypropyl methylcellulose, polyethylene oxide, polyoxypropylene, polyvinylpyrrolidone, carbomer, sodium carboxymethyl starch, carboxymethyl cellulose and sodium salt thereof or cross-linked carboxymethyl cellulose sodium or a combination thereof.

The sustained release oral dosage form of the present invention may also include various pharmaceutically acceptable excipients, for example disintegrants such as starch, cellulose derivatives, gums, crosslinked polymers and the like; binders such as starch, gelatin, sugars, cellulose derivatives, polyvinylpyrrolidone and the like; lubricants such as talc, magnesium stearate, colloidal silicon dioxide, polyethylene glycol, cellulose derivatives and the like; preservatives such as ascorbic acid, citric acid, butylhydroxytoluene, butylhydroxyanisole, propyl gallate and the like; controlled-release agent such as hydrophilic cellulose derivatives, carbomer, polyvinylpyrrolidone and the like; and mixtures thereof.

The tablet core may also contain a colorant. The use of a colorant can facilitate to identify the drug compartment and the push compartment. However, the color of the drug compartment and the push compartment is inconsequential, and color selection does not influence the usage and effect of the present invention. The colorants can be one or more selected from the group consisting of iron oxide red, iron oxide yellow, iron oxide purple, iron oxide black, titanium oxide and mixture thereof. In one embodiment, the colorant takes up 0 to 2%, preferably 0.1 to 1.5%, in the drug compartment, based on the total weight of the drug compartment. In another embodiment, the colorant takes up 0 to 2%, preferably 0.1 to 1.5%, in the push compartment, based on the total weight of the push compartment.

The tablet core is coated with a semipermeable membrane containing at least one coating material. The coating material is dissolved or suspended in an appropriate solvent or a mixture of solvents and sprayed on the tablet core for coating. The coating materials may be selected from the group consisting of cellulose acetate, cellulose diacetate, cellulose triacetate, ethylcellulose, cellulose acrylate, cellulose diacrylate and cellulose triacrylate or a combination thereof. The coating level can vary from 1% to 25%, preferably from 2% to 20%, and most preferably from 3% to 10% by weight of tablet core.

The semipermeable membrane preferably also contains at least one plasticizer to improve flexibility and durability of the coat. Such plasticizers include, but are not limited to, triethyl citrate, propylene glycol, or mixtures thereof in ratios of triethyl citrate to propylene glycol ranging from 25:75 to 75:25, Tween 80, polyethylene glycols, other polyethylene oxide sorbitan esters, triacetin, diethyl phthalate, mineral oil, tributyl sebacate, and glycerol. The semipermeable membrane optionally contains a permeation enhancing agent, such as pore forming agent. The pore forming agents cause the formation of microporous membrane which regulates the fluid penetration ability and also the drug release rate. The pore forming agent may be selected from the group consisting of hydroxypropyl cellulose, hydroxypropyl methylcellulose, methylcellulose, glycerol, propylene glycol, polyethylene glycol, sucrose, mannitol, lactose, sodium chloride or a combination thereof.

The sustained release oral dosage form further includes at least one passageway which is located at the semipermeable membrane to provide osmotic delivery of the drug. In general, the at least one passageway has a diameter of from 50 μm to 1000 μm, preferably from 100 μm to 800 μm. The passageway is formed by drilling using a laser or any other appropriate hole drilling system. Alternatively, the passageway is formed in situ during tableting process by tooling, or is formed in situ after contact with fluid. The passageway can have any shape such as round, triangular, square, elliptical, and the like. The various shapes contemplated for this invention include but are not limited to round, cross-shaped, rectangular, diamond, star, and square shapes. The osmotic agent in the tablet core draws water into the tablet core creating an osmotic gradient across the semipermeable membrane. The osmotic gradient pushes the drug in the solution out through the passageway.

The sustained release oral dosage form optionally comprises a cosmetic film coated onto the surface of semipermeable membrane. Besides, the sustained release oral dosage form optionally comprises a seal coat coated onto the surface of tablet core.

The sustained release oral dosage form comprising dalfampridine provides the drug plasma concentration at about 5 to 100 ng/mL for about 3 to 18 hours or at about 5 to 100 ng/mL for about 3 to 21 hours after oral administration. In some embodiments of present invention, the oral dosage form provides the drug plasma concentration at about 10 to 30 ng/mL for about 15 to 21 hours after oral administration.

The sustained release oral dosage form comprising dalfampridine to treat various neurological diseases, such as spinal cord injury, Alzheimer's disease, multiple sclerosis, amyotrophic lateral sclerosis or post-stroke deficiency, provides a flattened drug plasma profile ranged from about 5 to 100 ng/mL for about 3 to 18 hours or at about 5 to 100 ng/mL for about 3 to 21 hours after administration and then the plasma concentration decreases to not more than 50 ng/mL, 40 ng/mL, 30 ng/mL, 20 ng/mL, or 10 ng/mL at 24 hours post dosing. In some embodiments, it provides a flattened drug plasma profile ranged from about 10 to 30 ng/mL for about 15 to 21 hours after administration. The oral dosage form optionally has an initial lag phase of drug release less than 2 hours after oral administration. The dosage form may additionally comprise an immediate-release drug overcoat to minimize the lag phase by providing an initial drug burst.

The sustained release oral dosage form for administration in once daily regimen reduces the risk of seizure or other potential adverse effects associated with inappropriate schedule of drug administration of AMPYRA®. Moreover, the sustained release oral dosage form improves patient compliance and enhances therapeutic effect.

In some embodiments of present invention, the oral dosage form provides prolonged release of the drug for at least 18 hours, preferably at least 20 hours, and more preferably at least 24 hours.

In some embodiments of present invention, the oral dosage form comprising 10 mg to 30 mg dalfampridine provides a $C_{max}$ which is not more than 100 ng/mL, 75 ng/mL, 50 ng/mL, 35 ng/mL, 30 ng/mL, or 25 ng/mL. In another embodiment, the oral dosage form comprising 10 mg to 20 mg dalfampridine provides a $C_{max}$ which is not more than 100 ng/mL, 75 ng/mL, 50 ng/mL, 35 ng/mL, 30 ng/mL, or 25 ng/mL. Moreover, the time to the maximum concentration ($T_{max}$) of oral dosage form in the plasma of a patient following administration of a dose is 8 hours or more than 8 hours.

In some embodiments of present invention, the oral dosage form provides a fluctuation index about 1.5 or less, more preferably within the range of 0 to 1.0. The fluctuation index is calculated by "$(C_{max,ss} - C_{min,ss})/C_{av,ss}$", wherein $C_{max,ss}$ means steady-state peak plasma concentration, $C_{min,ss}$ means steady-state minimum plasma concentration, and $C_{av,ss}$ means steady-state average plasma concentration within a dosing interval $\tau$ and is calculated by "$AUC_{\tau,ss}/\tau$". In another embodiment, the oral dosage form provides a ratio of "$(C_{max,ss} - C_{min,ss})$/dosing strength" that is not more than 3.5, 3.0, 2.5, 2.0, 1.5, 1.0, or 0.5.

In some embodiments of present invention, the oral dosage form comprising 10 mg to 30 mg of dalfampridine provides an $AUC_{0-inf}$ in the range of 150 to 750 ng·h/mL, particularly in the range of 300 to 650 ng·h/mL and more particularly in the range of 300 to 500 ng·h/mL. In another embodiment, the oral dosage form comprising 10 mg to 20 mg of dalfampridine provides an $AUC_{0-inf}$ in the range of 150 to 750 ng·h/mL, particularly in the range of 300 to 650 ng·h/mL and more particularly in the range of 300 to 500 ng·h/mL. In a preferred embodiment, the oral dosage form has a similar $C_{max}$ and/or $AUC_{0-24}$ as AMPYRA® twice daily, more specifically, the 90% confidence intervals of the geometric mean ratio for the $C_{max}$ and/or $AUC_{0-24}$ metrics fall within the limits of 80% to 125% between the present dosage form and AMPYRA®.

In some embodiments of present invention, the drug absorption of the oral dosage form is not affected or less affected when it is taken with food. Specifically, the 90% confidence intervals of the geometric mean ratio for the $C_{max}$ and/or $AUC_{0-24}$ metrics fall within the limits of 80% to 125% between fasting and fed conditions, as measured in a single-dose human pharmacokinetic study.

In one embodiment, the oral dosage form has no or less dose dumping effect caused by alcohol. Specifically, the drug release form has no or less dose dumping effect within testing conditions of a suitable medium containing ethanol assayed in USP Type II dissolution apparatus, wherein the suitable medium is hydrochloride, water, phosphate buffer, or a dissolution medium recommended in USP, and the incorporated ethanol is presented in the range of 5% to 40% (v/v).

EXAMPLES

Example 1

A sustained release oral dosage form comprising a tablet core with two compartments was provided. The oral dosage form was in accord with conventional manufacturing processes known in the art. As shown in TABLE 1, the drug compartment of tablet core containing dalfampridine, polyethylene oxide, polyvinylpyrrolidone and magnesium stearate was prepared by wet granulation methods to form the first granule, and the push compartment of tablet core containing polyethylene oxide, sodium chloride, polyvinylpyrrolidone, ferric chloride, magnesium stearate and butylated hydroxytoluene was prepared by wet granulation methods to form the second granule. Then, the granulation preparations of those two granules were longitudinally compressed together to form a bi-layer tablet core. A semipermeable membrane comprising cellulose acetate and polyethylene glycol was prepared by dissolving the ingredients in a cosolvent comprising acetone and water in a ratio of 90:10 by weight composition to make a 4% solid solution and then was sprayed onto the bi-layer tablet core. The coating level is about 10.8% by weight of tablet core. Finally, a passageway with a diameter of 500 μm on the drug compartment side was formed by laser drill.

TABLE 1

| | Components | Weight (mg) | Percentage (% w/w) |
|---|---|---|---|
| Drug Compartment | Dalfampridine | 27.05 | 18.40 |
| | Polyethylene oxide 200K | 111.72 | 76.00 |
| | Polyvinylpyrrolidone K30 | 7.35 | 5.00 |
| | Magnesium stearate | 0.88 | 0.60 |
| | Total | 147 | 100 |
| Push Compartment | Polyethylene oxide 7500K | 62.40 | 63.67 |
| | Sodium chloride | 29.40 | 30.00 |
| | Polyvinylpyrrolidone K30 | 4.90 | 5.00 |
| | Ferric chloride | 0.98 | 1.00 |
| | Magnesium stearate | 0.24 | 0.25 |
| | Butylated hydroxytoluene | 0.08 | 0.08 |
| | Total | 98 | 100 |

TABLE 1-continued

| | Components | Weight (mg) | Percentage (% w/w) |
|---|---|---|---|
| Semipermeable Membrane | Cellulose acetate 398 | 25.08 | 95.00 |
| | Polyethylene glycol 3350 | 1.32 | 5.00 |
| | Total | 26.4 | 100 |

Example 2

A sustained release oral dosage form comprising a tablet core with two compartments was provided. TABLE 2 shows that the drug compartment of tablet core contains dalfampridine, polyethylene oxide, sorbitol, hydroxypropyl methylcellulose, magnesium stearate and butylated hydroxytoluene, and the push compartment contains polyethylene oxide, sodium chloride, hydroxypropyl methylcellulose, ferric oxide, magnesium stearate and butylated hydroxytoluene. They were separately prepared following similar procedures described in Example 1 and to form a bi-layer tablet core. A semipermeable membrane comprising cellulose acetate and polyethylene glycol was prepared by dissolving the ingredients in a cosolvent comprising acetone and water in a ratio of 90:10 by weight composition to make a 4% solid solution and then was sprayed onto the bi-layer tablet core. The coating level is about 17.4% by weight of tablet core. Finally, a passageway with a diameter of 760 μm on the drug compartment side was formed by laser drill.

TABLE 2

| | Components | Weight (mg) | Percentage (% w/w) |
|---|---|---|---|
| Drug Compartment | Dalfampridine | 14.08 | 12.80 |
| | Polyethylene oxide 200K | 60.22 | 54.75 |
| | Sorbitol | 27.94 | 25.40 |
| | Hydroxypropyl methylcellulose K4M | 2.20 | 2.00 |
| | Magnesium stearate | 5.50 | 5.00 |
| | Butylated hydroxytoluene | 0.06 | 0.05 |
| | Total | 110 | 100 |
| Push Compartment | Polyethylene oxide 7000K | 71.08 | 53.85 |
| | Sodium chloride | 52.80 | 40.00 |
| | Hydroxypropyl methylcellulose K4M | 6.00 | 5.00 |
| | Ferric oxide | 1.32 | 1.00 |
| | Magnesium stearate | 0.13 | 0.10 |
| | Butylated hydroxytoluene | 0.07 | 0.05 |
| | Total | 132 | 100 |
| Semipermeable Membrane | Cellulose acetate 398 | 19.95 | 47.50 |
| | Cellulose acetate 320 | 19.95 | 47.50 |
| | Polyethylene glycol 3350 | 2.10 | 5.00 |
| | Total | 42 | 100 |

Example 3

A sustained release oral dosage form comprising a tablet core with two compartments was provided and made using processes according to the above examples. In this example, the components of oral dosage form are shown in TABLE 3. The semipermeable membrane weighed 19.00 mg. Moreover, the diameter of a passageway was 350 μm.

TABLE 3

| | Components | Weight (mg) | Percentage (% w/w) |
|---|---|---|---|
| Drug Compartment | Dalcampridine | 14.10 | 16.3 |
| | Polyethylene oxide 200K | 70.24 | 76.35 |
| | Sodium chloride | 4.60 | 5.00 |
| | Hydroxypropyl methylcellulose K4M | 1.84 | 2.00 |
| | Magnesium stearate | 0.23 | 0.25 |
| | Butylated hydroxytoluene | 0.07 | 0.08 |
| | Black iron oxide/lactose (95:5) | 0.02 | 0.02 |
| | Total | 92 | 100 |
| Push Compartment | Polyethylene oxide 2000K | 39.48 | 63.67 |
| | Sodium chloride | 18.60 | 30.00 |
| | Hydroxypropyl methylcellulose K4M | 3.10 | 5.00 |
| | Magnesium stearate | 0.155 | 0.25 |
| | Butylated hydroxytoluene | 0.05 | 0.08 |
| | Black iron oxide/lactose (95:5) | 0.62 | 1.00 |
| | Total | 62 | 100 |
| Semipermeable Membrane | Cellulose acetate 398 | 18.81 | 99.00 |
| | Polyethylene glycol 3350 | 0.19 | 1.00 |
| | Total | 19 | 100 |

Example 4

A sustained release oral dosage form comprising a tablet core with two compartments was provided and prepared using processes according to the above examples. In this example, the components of oral dosage form are shown in TABLE 4. The semipermeable membrane weighed 35.60 mg. Moreover, the diameter of a passageway was 630 μm.

TABLE 4

| | Components | Weight (mg) | Percentage (% w/w) |
|---|---|---|---|
| Drug Compartment | Dalfampridine | 9.97 | 13.60 |
| | Polyethylene oxide 200K | 54.24 | 74.00 |
| | Sodium chloride | 5.72 | 7.80 |
| | Polyvinylpyrrolidone K30 | 2.56 | 3.50 |
| | Magnesium stearate | 0.81 | 1.10 |
| | Total | 73.3 | 100 |
| Second Compartment | Polyethylene oxide 7000K | 40.30 | 54.97 |
| | Sodium chloride | 27.52 | 37.55 |
| | Hydroxypropyl methylcellulose K4M | 2.38 | 3.25 |
| | Magnesium stearate | 0.35 | 0.47 |
| | Polyvinylpyrrolidone K30 | 2.10 | 2.86 |
| | Ferric oxide | 0.65 | 0.89 |
| | Total | 73.3 | 100 |
| Semipermeable Membrane | Cellulose acetate 398 | 32.57 | 91.50 |
| | Polyethylene glycol 3350 | 3.03 | 8.50 |
| | Total | 35.6 | 100 |

Example 5-6

Two sustained release oral dosage forms comprising a tablet core with two compartments were provided and prepared using processes according to the above examples. The components of each component of oral dosage form are shown in TABLE 5. Regarding to the semipermeable membrane, the coating levels were about 20.0% and 14.7% by weight of tablet core. Moreover, the diameters of a passageway in these two examples were 500 μm.

TABLE 5

| | | Example 5 | | Example 6 | |
|---|---|---|---|---|---|
| | Components | Weight (mg) | Percentage (% w/w) | Weight (mg) | Percentage (% w/w) |
| Drug Compartment | Dalfampridine | 10.00 | 10.00 | 10.00 | 10.00 |
| | Polyethylene oxide 200K | 65.42 | 65.42 | 71.35 | 71.35 |
| | Hydroxypropyl methylcellulose K4M | 7.76 | 7.76 | 8.47 | 8.47 |
| | Sodium chloride | 13.27 | 13.27 | 6.63 | 6.63 |
| | Polyvinylpyrrolidone K30 | 2.62 | 2.62 | 2.62 | 2.62 |
| | Magnesium stearate | 0.93 | 0.93 | 0.93 | 0.93 |
| | Total | 100 | 100 | 100 | 100 |
| Second Compartment | Polyethylene oxide 4000K | 44.60 | 63.71 | 54.78 | 78.75 |
| | Sodium chloride | 20.97 | 29.95 | 10.49 | 14.98 |
| | Hydroxypropyl methylcellulose K15M | 1.33 | 1.90 | 1.63 | 2.33 |
| | Magnesium stearate | 0.11 | 0.16 | 0.11 | 0.16 |
| | Polyvinylpyrrolidone K30 | 2.22 | 3.17 | 2.22 | 3.17 |
| | Ferric oxide | 0.77 | 1.11 | 0.77 | 1.11 |
| | Total | 70 | 100 | 70 | 100 |
| Semipermeable Membrane | Cellulose acetate 398 | 32.30 | 95.00 | 23.78 | 95.10 |
| | Polyethylene glycol 3350 | 1.70 | 5.00 | 1.23 | 4.90 |
| | Total | 34 | 100 | 25 | 100 |

Example 7

A sustained release oral dosage form comprising a tablet core with two compartments was provided. TABLE 6 shows that the drug compartment of tablet core contains dalfampridine, polyethylene oxide, hydroxypropyl methylcellulose, magnesium stearate and sodium chloride, and the push compartment contains polyethylene oxide, sodium chloride, hydroxypropyl methylcellulose, ferric oxide and magnesium stearate. They were separately prepared following the similar procedures described in Example 1 and to form a bi-layer tablet core. Regarding tp the semipermeable membrane, the coating level was about 15.0% by weight of tablet core. Moreover, the diameter of a passageway was 450 μm.

TABLE 6

| | Components | Weight (mg) | Percentage (% w/w) |
|---|---|---|---|
| Drug Compartment | Dalfampridine | 10.00 | 10.00 |
| | Polyethylene oxide 200K | 62.70 | 62.70 |
| | Hydroxypropyl methylcellulose K4M | 9.74 | 9.74 |
| | Ethylcellulose 10 | 10.00 | 10.00 |
| | Sodium chloride | 6.63 | 6.63 |
| | Magnesium stearate | 0.93 | 0.93 |
| | Total | 100 | 100 |
| Second Compartment | Polyethylene oxide 4000K | 52.30 | 74.71 |
| | Sodium chloride | 10.49 | 14.98 |
| | Hydroxypropyl methylcellulose K15M | 6.33 | 9.04 |
| | Magnesium stearate | 0.11 | 0.16 |
| | Ferric oxide | 0.77 | 1.11 |
| | Total | 70 | 70 |
| Semipermeable Membrane | Cellulose acetate 398 | 24.20 | 94.90 |
| | Polyethylene glycol 3350 | 1.30 | 5.10 |
| | Total | 25.5 | 100 |

Example 8

A sustained release oral dosage form comprising a tablet core with two compartments was provided. TABLE 7 shows that the drug compartment of tablet core contains dalfampridine, polyethylene oxide, hydroxypropyl methylcellulose, polyvinylpyrrolidone, magnesium stearate and sodium chloride, and the push compartment contains polyethylene oxide, sodium chloride, hydroxypropyl methylcellulose, ferric oxide, polyvinylpyrrolidone and magnesium stearate. They were separately prepared following the similar procedures described in Example 1 and to form a bi-layer tablet core. The semipermeable membrane weighed 25.5 mg. Moreover, the diameter of a passageway was 500 μm.

TABLE 7

| | Components | Weight (mg) | Percentage (% w/w) |
|---|---|---|---|
| Drug Compartment | Dalfampridine | 10.00 | 10.00 |
| | Polyethylene oxide 200K | 71.36 | 71.36 |
| | Hydroxypropyl methylcellulose K4M | 8.46 | 8.46 |
| | Sodium chloride | 6.64 | 6.64 |
| | Polyvinylpyrrolidone K30 | 2.62 | 2.62 |
| | Magnesium stearate | 0.93 | 0.93 |
| | Total | 100 | 100 |
| Second Compartment | Polyethylene oxide 4000K | 44.60 | 63.71 |
| | Hydroxypropyl methylcellulose K15M | 1.33 | 1.90 |
| | Sodium chloride | 20.97 | 29.95 |
| | Magnesium stearate | 0.11 | 0.16 |
| | Polyvinylpyrrolidone K30 | 2.22 | 3.17 |
| | Ferric oxide | 0.77 | 1.11 |
| | Total | 70 | 70 |
| Semipermeable Membrane | Cellulose acetate 398 | 24.20 | 94.90 |
| | Polyethylene glycol 3350 | 1.30 | 5.10 |
| | Total | 25.5 | 100 |

Example 9

A sustained release oral dosage form comprising a tablet core with one compartment was provided. The oral dosage form was in accord with conventional manufacturing processes known in the art. As shown in TABLE 8, the tablet core contains dalfampridine, xanthan gum, copovidone, sodium chloride, sodium bicarbonate, sodium carboxy methyl starch, aerosol and magnesium stearate. Xanthan gum, sodium chloride, sodium bicarbonate and sodium carboxy methyl starch were mixed together and then wet-granulated with a solution of dalfampridine and copovidone in water. The granules were then mixed with aerosil and magnesium stearate. The mixture was subsequently compressed into tablet core by compression tooling. The tablet cores were coated with a coating solution containing the components of the semipermeable membrane. The coated tablet cores were subsequently dried. Two passageways, each with a diameter of approximate 600 μm, were subsequently made into each tablet with a hand drill.

TABLE 8

| | Components | Weight (mg) | Percentage (% w/w) |
|---|---|---|---|
| Tablet Core | Dalfampridine | 30.0 | 18.3 |
| | Xanthan gum | 51.0 | 31.1 |
| | Copovidone | 29.5 | 18.0 |
| | Sodium chloride | 29.0 | 17.7 |
| | Sodium bicarbonate | 10.2 | 6.2 |
| | Sodium carboxy methyl starch | 12.9 | 7.9 |
| | Aerosol | 0.9 | 0.5 |
| | Magnesium stearate | 0.5 | 0.3 |
| | Total | 164 | 100 |
| Semipermeable Membrane | Cellulose acetate 398 | 7.5 | 94.9 |
| | Polyethylene glycol 3350 | 0.4 | 5.1 |
| | Total | 7.9 | 100 |

Example 10

A sustained release oral dosage form comprising a tablet core with one compartment was provided. The oral dosage form was in accord with conventional manufacturing processes known in the art. As shown in TABLE 9, the tablet core contains dalfampridine, polyethylene oxide, hydroxypropyl methylcellulose, polyvinylpyrrolidone, sodium chloride and magnesium stearate. Dalfampridine, polyethylene oxide, hydroxypropyl methylcellulose, sodium chloride were mixed together and then wet-granulated with a polyvinylpyrrolidone ethanol solution. The granules were then mixed with magnesium stearate. The mixture was subsequently compressed into tablet core by compression tooling. A semipermeable membrane comprising cellulose acetate and polyethylene glycol was prepared by dissolving the ingredients in a cosolvent comprising acetone and water in a ratio of 90:10 by weight composition to make a 4% solid solution and then was sprayed onto the tablet core. The coating level was about 14.7% by weight of tablet core. Finally, a passageway with a diameter of 520 μm was formed by laser drill.

TABLE 9

|  | Components | Weight (mg) | Percentage (% w/w) |
|---|---|---|---|
| Tablet Core | Dalfampridine | 17.00 | 10.00 |
|  | Polyethylene oxide N80 | 121.30 | 71.35 |
|  | Hydroxypropyl methylcellulose K4M | 14.40 | 8.47 |
|  | Sodium chloride | 11.27 | 6.63 |
|  | Polyvinylpyrrolidone K30 | 4.45 | 2.62 |
|  | Magnesium stearate | 1.58 | 0.93 |
|  | Total | 170 | 100 |

TABLE 9-continued

|  | Components | Weight (mg) | Percentage (% w/w) |
|---|---|---|---|
| Semipermeable Membrane | Cellulose acetate 398 | 24.20 | 94.90 |
|  | Polyethylene glycol 3350 | 1.30 | 5.10 |
|  | Total | 25.5 | 100 |

Example 11-12

Two sustained release oral dosage forms comprising a tablet core with three compartments were provided. The oral dosage form was in accord with conventional manufacturing processes known in the art. As shown in TABLE 10, the drug compartment contains dalfampridine, polyethylene oxide, hydroxypropyl methylcellulose, sodium chloride, polyvinylpyrrolidone and magnesium stearate, the push compartment contains polyethylene oxide, sodium chloride, hydroxypropyl methylcellulose, magnesium stearate, polyvinylpyrrolidone and ferric oxide, and the polymer compartment contains hydroxypropyl methylcellulose and ethylcellulose were prepared by wet granulation method to form different granules. Then, the granules were longitudinally compressed together to form a tri-layer tablet core which the third component was located between the other two components. A semipermeable membrane comprising cellulose acetate and polyethylene glycol was prepared by dissolving the ingredients in a cosolvent comprising acetone and water in a ratio of 90:10 by weight composition to make a 4% solid solution and then was sprayed onto the tri-layer tablet core. The coating level was about 12.5% by weight of tablet core. Finally, a passageway with a diameter of 500 μm on the drug compartment side was formed by laser drill.

TABLE 10

|  |  | Example 11 | | Example 12 | |
|---|---|---|---|---|---|
|  | Components | Weight (mg) | Percentage (% w/w) | Weight (mg) | Percentage (% w/w) |
| Drug Compartment | Dalfampridine | 10.00 | 10.00 | 10.00 | 10.00 |
|  | Polyethylene oxide 200K | 65.42 | 65.42 | 71.35 | 71.35 |
|  | Hydroxypropyl methylcellulose K4M | 7.76 | 7.76 | 8.47 | 8.47 |
|  | Sodium chloride | 13.27 | 13.27 | 6.63 | 6.63 |
|  | Polyvinylpyrrolidone K30 | 2.62 | 2.62 | 2.62 | 2.62 |
|  | Magnesium stearate | 0.93 | 0.93 | 0.93 | 0.93 |
|  | Total | 100 | 100 | 100 | 100 |
| Push Compartment | Polyethylene oxide 4000K | 44.60 | 63.71 | 54.78 | 78.25 |
|  | Sodium chloride | 20.97 | 29.95 | 10.49 | 14.98 |
|  | Hydroxypropyl methylcellulose K15M | 1.33 | 1.90 | 1.63 | 2.33 |
|  | Magnesium stearate | 0.11 | 0.16 | 0.11 | 0.16 |
|  | Polyvinylpyrrolidone K30 | 2.22 | 3.17 | 2.22 | 3.17 |
|  | Ferric oxide | 0.77 | 1.11 | 0.77 | 1.11 |
|  | Total | 70 | 100 | 70 | 100 |
| Polymer Compartment | Hydroxypropyl methylcellulose K100M | 30.0 | 100.0 | 24.0 | 80.0 |
|  | Ethylcellulose 10 | — | — | 6.0 | 20.0 |
|  | Total | 30 | 100 | 30 | 100 |

TABLE 10-continued

|  | | Example 11 | | Example 12 | |
| --- | --- | --- | --- | --- | --- |
| | Components | Weight (mg) | Percentage (% w/w) | Weight (mg) | Percentage (% w/w) |
| Semipermeable Membrane | Cellulose acetate 398 | 24.20 | 94.90 | 24.20 | 94.90 |
| | Polyethylene glycol 3350 | 1.30 | 5.10 | 1.30 | 5.10 |
| | Total | 25.5 | 100 | 25.5 | 100 |

[Dissolution Test]

Dissolution tests of Example 5 to 8, 10 and 12 were performed like the method as mentioned above. The oral dosage forms were placed in a USP Type 11 (paddle) dissolution apparatus and immersed in about 500 mL of purified water equilibrated in a constant temperature water bath at 37° C.±0.5° C. Aliquots of the sample solutions were injected into a chromatographic system to quantify the amounts of drug released during the testing intervals. The test results were shown in TABLE 11.

TABLE 11

Dalfampridine release (% w/w) as a function of time Example 5-8, 10 and 12

| Time (hours) | 5 | 6 | 7 | 8 | 10 | 12 |
| --- | --- | --- | --- | --- | --- | --- |
| 0 | 0 | 0 | 0 | 0 | 0 | 0 |
| 1 | 0 | 0.79 | 0.59 | 0 | 2.75 | 0.33 |
| 1.5 | 0.37 | 5.08 | 3.95 | 0 | 4.81 | 3.75 |
| 2 | 2.28 | 10.69 | 8.79 | 0.61 | 7.40 | 8.72 |
| 3 | 10.54 | 20.60 | 20.75 | 4.45 | 11.66 | 18.58 |
| 4 | 18.94 | 29.27 | 29.99 | 9.95 | 16.54 | 28.74 |
| 6 | — | — | 45.47 | 18.66 | 29.87 | 45.37 |
| 8 | 45.62 | 52.90 | 60.09 | 26.40 | 40.63 | 59.86 |
| 12 | 64.72 | 64.69 | 79.88 | 38.89 | 56.98 | 80.50 |
| 18 | 81.62 | 73.66 | 89.43 | 51.84 | 70.94 | 88.76 |
| 26 | — | 84.81 | 96.61 | 63.13 | 83.20 | 97.38 |
| 32 | 94.78 | — | — | — | — | — |

[Pharmacokinetic Simulation]

Simulation was performed to extrapolate pharmacokinetic profiles of human subjects using dissolution data obtained from Examples. Convolution using technique known in the art provided the conversion of release profile (input) into plasma concentration profile (output). The pharmacokinetics model used to describe the data was a one-compartment PK model with first-order absorption. Parameters in the model included absolute bioavailability of oral dosage forms (F), absorption rate constant (ka), volume of distribution (V, standardized to the weight of 75 kg) and elimination rate constant (ke). The above parameters were obtained from literatures, except ka, which was estimated from the model. The predictability of the model was verified comparing the data simulated with those reported in literatures and was found adequate to describe the pharmacokinetic profiles of dalfampridine in human subjects. Moreover, steady-state pharmacokinetic profiles were then simulated based on modeling data. The results were shown in TABLE 12. From this we simulated that human subjects were administered a single and/or multiple dose of from 17.5 to 30.0 mg of dalfampridine. The simulation predicted the duration for human subject maintaining the drug plasma concentration at about 10 to 30 ng/mL for about 17.5 hours to 21.0 hours after administration. The human subjects maintain the $C_{max}$ from 23.4 ng/mL to 28.2 ng/mL which is less than 30 ng/mL and the $T_{max}$ is about 8 hours or more than 8 hours. Moreover, the $AUC_{0-inf}$ are within a range from about 300 ng·h/mL to about 750 ng·h/mL. Furthermore, the fluctuation index of plasma concentration was calculated to be not more than 1.5, and not more than 1.0 in some examples.

TABLE 12

Simulated PK parameters for oral dosage form containing dalfampridine, Example 5-8, 10 and 12

| | 5 | 6 | 7 | 8 | 10 | 12 |
| --- | --- | --- | --- | --- | --- | --- |
| Dose (mg) | 20.0 | 20.5 | 17.5 | 29.0 | 24.5 | 17.5 |
| Duration (hr) | 20.5 | 19.5 | 18.0 | 20.0 | 21.0 | 17.5 |
| $C_{max}$ (ng/mL) | 26.1 | 27.9 | 28.1 | 23.4 | 27.4 | 28.2 |
| $T_{max}$ (hr) | 8.5 | 8 | 8 | 12 | 8 | 8 |
| $AUC_{0-inf}$ (ng·h/mL) | 530.7 | 664.7 | 499.5 | 747.7 | 741.7 | 520.4 |
| $C_{max, ss}$ (ng/mL) | 28.4 | 30.0 | 29.8 | 25.4 | 30.3 | 29.9 |
| $C_{min, ss}$ (ng/mL) | 8.4 | 8.5 | 6.6 | 10.2 | 13.2 | 6.6 |
| Fluctuation index | 1.0 | 1.1 | 1.2 | 0.8 | 0.8 | 1.2 |
| $(C_{max, ss} - C_{min, ss})$/dosing strength | 1.0 | 1.0 | 1.3 | 0.5 | 0.7 | 1.3 |

[Alcohol-Induced Dose Dumping Test]

According to USFDA (Presentations at the Pharmaceutical Sciences Advisory Committee Meeting Oct. 26, 2005), an in vivo pharmacokinetic study examining whether there is an alcohol-formulation interaction is not the preferred approach due to potential risk to human. In order to observe the sustained release oral dosage form has no or less dose dumping effect caused by alcohol, an in vitro alcohol-induced dose dumping test was conducted using 0.1 N HCl with and without 40% (v/v) of ethanol USP. FDA is proposing classifying formulations into three groups: rugged, vulnerable and uncertain. In FDA's example of a vulnerable formulation, the drug release from a formulation dissolved in 40% ethanol is actually exaggerated compared to a control formulation dissolved in a medium without ethanol, e.g. the drug release more than 60% (w/w) within an hour or the drug release more than 80% (w/w) within 2 hours. As shown in TABLE 13, our data was collected every 15 minutes for a total of two hours. From the result, the oral dosage form of the present invention did not show the exaggerated release of a drug in 0.1 N HCl with 40% (v/v) ethanol, more specifically, dalfampridine release less than 25% (w/w) within an hour and less than 40% (w/w) within 2 hours. Therefore, there is no dose dumping effect caused by alcohol in the present invention.

TABLE 13

Dalfampridine release (% w/w) as a function of time, Example 6

| Time (Minutes) | Without ethanol | With 40% (v/v) ethanol |
| --- | --- | --- |
| 0 | 0.0 | 0.0 |
| 15 | 3.02 | 8.08 |

TABLE 13-continued

Dalfampridine release (% w/w) as a function of time, Example 6

| Time (Minutes) | Without ethanol | With 40% (v/v) ethanol |
|---|---|---|
| 30 | 4.85 | 12.59 |
| 45 | 7.28 | 19.04 |
| 60 | 11.03 | 24.16 |
| 75 | 15.14 | 28.46 |
| 90 | 19.38 | 31.16 |
| 105 | 22.46 | 34.14 |
| 120 | 25.63 | 36.57 |

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A sustained release oral osmotic tablet comprising:
   a tablet core which consisting essentially of: a drug compartment comprising dalfampridine, or a pharmaceutically acceptable salt thereof, sodium chloride, hydroxypropyl methylcellulose and pharmaceutically acceptable excipients, and wherein said dalfampridine is 5 to 30 mg and wherein the weight percent ratio of said sodium chloride in said drug compartment and said hydroxypropyl methylcellulose in said drug compartment is 0.78:1 to 1.7:1;
   a push compartment, comprising sodium chloride, hydroxypropyl methylcellulose and pharmaceutically acceptable excipients, and wherein the weight percent ratio of said hydroxypropyl methylcellulose in said drug compartment and said hydroxypropyl methylcellulose in said push compartment is 3.6:1 to 4.1:1;
   a semipermeable membrane, coating on said tablet core, a coating level of said semipermeable membrane is from about 2% to about 20% by weight of said tablet core, said semipermeable membrane comprises at least one cellulose and at least one plasticizer, said cellulose is selected from the group consisting of cellulose acetate, cellulose diacetate, cellulose triacetate, and a combination thereof;
   at least one passageway through said semipermeable membrane to said tablet core, and wherein said dalfampridine or the pharmaceutically acceptable salt to be delivered from said passageway; and
   wherein said sustained release oral osmotic tablet exhibits the following dissolution profile when placed in a USP type II apparatus in about 500 mL of purified water at about 37° C.:
   between 18.95% to 29.27% of said dalfampridine is released in 4 hours;
   between 45.62% to 52.90% of said dalfampridine is released in 8 hours; and
   between 73.66% to 81.62% of said dalfampridine is released in 18 hours.

2. The sustained release oral osmotic tablet according to claim 1, wherein said sodium chloride in said push compartment is from 15% to 30% by weight based on the total weight of said push compartment and said sodium chloride in said drug compartment is from 6.6% to 13.2% by weight based on the total weight of said drug compartment.

3. The sustained release oral osmotic tablet according to claim 1, wherein said hydroxypropyl methylcellulose in said drug compartment is from 7.8% to 8.5% by weight based on the total weight of said drug compartment and said hydroxypropyl methylcellulose in said push compartment is from 1.9% to 2.3% by weight based on the total weight of said push compartment.

4. The sustained release oral osmotic tablet according to claim 1, wherein said semipermeable membrane consist of 95% by weight of cellulose acetate and 5% by weight of polyethylene glycol.

5. The sustained release oral osmotic tablet according to claim 1, wherein said sustained release oral osmotic tablet comprising 65% to 71% by weight of polyethylene oxide based on the total weight of said drug compartment, and 64% to 78% by weight of polyethylene oxide based on the total weight of said push compartment.

6. The sustained release oral osmotic tablet according to claim 1, wherein said sustained release oral osmotic tablet comprising 2.6% by weight of polyvinylpyrrolidone based on the total weight of said drug compartment, and 3.2% by weight of polyvinylpyrrolidone based on the total weight of said push compartment.

7. The sustained release oral osmotic tablet according to claim 1, wherein said sustained release oral osmotic tablet in 0.1N HCl aqueous solution with 40% ethanol, compared to said sustained release oral osmotic tablet in 0.1N HCl aqueous solution without ethanol, exhibits a 1.4-fold difference in the average rate of release of the dalfampridine within 120 minutes.

8. The sustained release oral osmotic tablet according to claim 1, wherein said sustained release oral osmotic tablet in 0.1N HCl aqueous solution with 40% ethanol, compared to said sustained release oral osmotic tablet in 0.1N HCl aqueous solution without ethanol, exhibits a 2.5-fold difference in the average releasing rate of the dalfampridine within 0 to 60 minutes, and exhibits a 1.7-fold difference in the average releasing rate of the dalfampridine within 60 to 120 minutes.

9. The sustained release oral osmotic tablet according to claim 1, wherein the sustained release oral osmotic tablet is orally administered once daily and for the treatment of spinal cord injury, Alzheimer's disease, multiple sclerosis, amyotrophic lateral sclerosis or post-stroke deficiency.

10. The sustained release oral osmotic tablet according to claim 9, wherein said tablet provides the drug plasma concentration at about 10 to about 30 ng/mL for about 15 hours to about 21 hours after oral administration.

11. The sustained release oral osmotic tablet according to claim 9, wherein said tablet provides a $C_{max}$ less than 30 ng/mL.

12. The sustained release oral osmotic tablet according to claim 9, wherein said tablet provides a $T_{max}$ about 8 hours or more than 8 hours.

13. The sustained release oral osmotic tablet according to claim 9, wherein said tablet provides an $AUC_{0-inf}$ from about 300 ng·h/mL to about 750 ng·h/mL.

14. The sustained release oral osmotic tablet according to claim 9, wherein the fluctuation index of said tablet is not more than 1.5.

* * * * *